(12) United States Patent
Abrutyn

(10) Patent No.: US 6,719,966 B2
(45) Date of Patent: Apr. 13, 2004

(54) CREAMY, STABLE HOMOGENEOUS ANTIPERSPIRANT/DEODORANT COMPOSITION

(75) Inventor: Eric S. Abrutyn, Anderson, OH (US)

(73) Assignee: Andrew Jergens Company, Cincinnati, OH (US)

( * ) Notice: Subject to any disclaimer, the term of this patent is extended or adjusted under 35 U.S.C. 154(b) by 79 days.

(21) Appl. No.: 10/127,876

(22) Filed: Apr. 23, 2002

(65) Prior Publication Data

US 2003/0202949 A1 Oct. 30, 2003

(51) Int. Cl.$^7$ .............. A61K 7/32; A61K 7/34; A61K 7/38; A61K 31/74; A61K 7/00; A61K 35/78
(52) U.S. Cl. .............. 424/65; 424/66; 424/68; 424/78.02; 424/78.03; 424/400; 424/401; 424/725
(58) Field of Search .............. 424/65, 66, 68, 424/400, 401, 78.02, 78.03, 725

(56) References Cited

U.S. PATENT DOCUMENTS

| 4,937,069 A | 6/1990 | Shin |
| 5,254,332 A | 10/1993 | Grezcyn et al. |
| 5,292,530 A | 3/1994 | McCrea et al. |
| 5,531,986 A | 7/1996 | Shevade et al. |
| 5,885,559 A | 3/1999 | Lee et al. |
| 5,916,546 A | 6/1999 | Sawin et al. |
| 5,932,199 A | 8/1999 | Esser |
| 5,939,056 A | 8/1999 | Fletcher et al. |
| 5,976,514 A * | 11/1999 | Guskey et al. ............ 424/85 |
| 6,171,581 B1 | 1/2001 | Joshi et al. |
| 6,258,365 B1 | 7/2001 | LeGrow et al. |
| 6,261,543 B1 | 7/2001 | Fletcher et al. |

* cited by examiner

*Primary Examiner*—Shelley A. Dodson
(74) *Attorney, Agent, or Firm*—Frost Brown Todd LLC

(57) ABSTRACT

An antiperspirant/deodorant composition which includes a homogeneous wax-liquid matrix, minimizes syneresis or "creep," provides smooth skin emolliency and skin conditioning, minimizes white residue left on the skin, and promotes easier shaving with less irritation, is disclosed. The compositions include an antiperspirant or deodorant active selected from antiperspirant actives, deodorant actives, perfumes, and combinations thereof, a volatile fluid (such as dodecene or cyclomethicone), a wax structurant (such as behenyl alcohol), a $C_6$–$C_{45}$ alkyl-substituted polydimethylsiloxane, and a botanical extract (preferably a water-based botanical extract, such as ginger root extract). Preferred compositions are in the form of a semi-solid composition or a solid stick composition.

28 Claims, No Drawings

CREAMY, STABLE HOMOGENEOUS ANTIPERSPIRANT/DEODORANT COMPOSITION

TECHNICAL FIELD

The present invention relates to personal care antiperspirant and/or deodorant compositions, and particularly relates to cream, soft solid or solid antiperspirant/deodorant compositions which are applied topically to the skin.

BACKGROUND OF THE INVENTION

Deodorant and antiperspirant compositions are well-accepted and popular components of personal care and personal hygiene regimens. As a supplement to the periodic bathing of the body, these compositions counteract odors and prevent perspiration which can occur on the body between times that the body is washed. Deodorant and antiperspirant compositions are generally applied topically to the skin, for example in the underarm area, and there are a wide variety of composition types which can be used to do this. For example, solid sticks, soft solids, liquid roll-ons, cream compositions, and gel compositions, are but some of the forms which deodorant and antiperspirant compositions can take. The feel of a particular composition as it is applied to the skin (i.e., its perceived wetness and tackiness, as well as the smooth feeling which it leaves on the skin) is very important to the user and is frequently a determining factor in whether that composition will be re-purchased in the future.

The primary consumer benefit of an antiperspirant or deodorant product is clearly its antiperspirant or deodorant efficacy. However, in addition to such primary efficacy, the fact that a composition does not leave a white residue on the skin or clothing and also provides good skin feel are two very important cosmetic benefits of an antiperspirant or deodorant product. In addition to these residue and skin comfort issues, extrudable and solid stick antiperspirant and/or deodorant compositions typically formulated may also develop syneresis or "creep" of their volatile components. That phenomenon leaves an oily film on the dispensing container.

It would be very useful to have an efficacious antiperspirant or deodorant composition, formulated as a cream, soft solid or solid composition, based on a homogeneous wax-liquid matrix, which minimizes syneresis or creep, provides skin smooth emolliency and conditioning, provides good skin feel with minimized visible residue on the skin, and can permit easier shaving with less irritation. The present invention permits the incorporation of water (for example, that included in an aqueous-based botanical extract or other functional additive) into an anhydrous antiperspirant/deodorant system. This result is obtained, as described herein, by formulating a liquid antiperspirant/deodorant composition which includes an antiperspirant or deodorant active, a volatile fluid, a wax structurant, a $C_6$–$C_{45}$ alkyl-substituted polydimethylsiloxane, and a botanical extract (preferably a water-based botanical extract, such as ginger root extract).

U.S. Pat. No. 5,939,056, Fletcher, et al., issued Aug. 17, 1999, described substantially anhydrous cream antiperspirant/deodorant compositions which include an antiperspirant active, a carrier (such as a volatile silicone), a silica structurant, a $C_{14}$–$C_{22}$ alkyl methicone wax and, optionally, a wax structurant. The compositions are said to have improved efficacy and sensory properties. The compositions are substantially anhydrous and do not include water or water-based materials, such as water-based botanical extracts.

U.S. Pat. No. 5,976,514, Guskey, et al., issued Nov. 2, 1999, describes low irritation antiperspirant compositions which may be formulated as soft solid or solid sticks. The compositions may contain an antiperspirant active, a volatile, nonpolar hydrocarbon liquid (such as an Isopar material), and a skin irritation mitigating material (one example of which is taught to be $C_{24}$–$C_{28}$ alkyl methicone). Example 10 describes a solid composition containing 37.5% D5 cyclomethicone, 20% of an antiperspirant active, 5% of a silicone wax, 2.9% hydrogenated castor wax, 0.18% silica, 0.18% polyethylene, and 0.075% behenyl alcohol. The compositions are anhydrous; they do not contain any water-based material, and particularly do not contain botanical extracts.

U.S. Pat. No. 6,258,365 B1, LeGrow, et al., issued Jul. 10, 2001, describes gelled silicone materials for use in personal care products, such as antiperspirants. The silicone material includes a mixture of short chain alkylsiloxane materials together with alkyl silicone waxes, such as $C_{24}$–$C_{28}$ alkyl dimethicone.

U.S. Pat. No. 4,937,069, Shin, issued Jun. 26, 1990, describes semi-solid antiperspirant compositions which are said to be easily dispensed and exhibit good skin feel. The compositions may contain an antiperspirant active, a fumed silica thickening agent, a thickening/solid emollient (for example waxes, such as stearyl wax), a nonvolatile liquid emollient, and a volatile emollient, such as cyclomethicone. The disclosed compositions do not contain an alkyl-substituted polydimethylsiloxane material.

U.S. Pat. No. 5,531,986, Shevade, et al., issued Jul. 2, 1996, describes low residue antiperspirant solid stick compositions which may include an antiperspirant active, a volatile silicone fluid (such as cyclomethicone), a nonvolatile silicone fluid, dimethicone copolyol, a high melting point wax and a low melting point wax. The disclosed compositions do not include an alkyl-substituted polydimethylsiloxane.

U.S. Pat. No. 6,261,543 B1, Fletcher, et al., issued Jul. 17, 2001, describes antiperspirant emulsions which utilize a hydratable starch polymer to provide phase stability. The compositions may include cyclomethicone, $C_{10}$–$C_{30}$ alcohols and silica.

U.S. Pat. No. 5,932,199, Esser, issued Aug. 3, 1999, describes anhydrous antiperspirant stick compositions which may include an antiperspirant active, a carrier for the active (such as cyclomethicone), a structurant (such as $C_8$–$C_{30}$ alcohol), moisturizing cream, and a perfume carrier material (such as fumed silica). The compositions are not taught to include alkyl-substituted polydimethylsiloxanes or water-containing materials, such as botanical extracts.

U.S. Pat. No. 5,254,332, Grezcyn, et al., issued Oct. 19, 1993, describes antiperspirant compositions which may include a volatile silicone oil, such as cyclomethicone, a water insoluble liquid emollient (for example, diisopropyl adipate), a low melting point wax (for example, $C_8$–$C_{30}$ fatty alcohol), a coupling agent (such as PPG ethers of $C_{10}$–$C_{20}$ alcohols), an antiperspirant active and a deodorant active (such as sodium bicarbonate). The compositions are substantially anhydrous and are not taught to include alkyl-substituted polydimethylsiloxanes.

U.S. Pat. No. 5,292,530, McCrea, et al., issued Mar. 8, 1994, describes anhydrous antiperspirant compositions which can include an antiperspirant active, a volatile liquid carrier (such as cyclomethicone), a finely divided silica, and a suspending wax. The compositions are taught to provide good cosmetic properties with reduced syneresis. Once again, the compositions are substantially anhydrous and are not taught to include alkyl-substituted polydimethylsiloxanes.

U.S. Pat. No. 5,885,559, Lee, et al., issued Mar. 23, 1999, describes antiperspirant compositions in the form of a cream or soft solid which can comprise an antiperspirant active, a volatile silicone (such as cyclomethicone), a linear chain silicone, and a hexanediol-behenyl beeswax gelling agent. The composition is taught to eliminate the need for conventional gelling agents, such as fatty alcohols or hydrogenated castor oil.

U.S. Pat. No. 6,171,581 B1, Joshi, et al., issued Jan. 9, 2001, describes antiperspirant compositions in the form of a solid or soft solid water and oil emulsion. The compositions can include a silicone elastomer, a gellant, an antiperspirant active, water, and oil. While the silicone elastomer component is broadly defined, it does not include alkyl-substituted polydimethylsiloxanes. The gellant material disclosed may include behenyl alcohol; the oil may be a cyclomethicone.

U.S. Pat. No. 5,916,546, Sawin, et al., issued Jun. 29, 1999, describes antiperspirant stick compositions which are said to provide good skin feel and low visible skin residue. The compositions can comprise an antiperspirant active, a solidifying agent (such as waxes or fatty alcohols), a volatile emollient (such as cyclomethicone), a non-volatile silicone or hydrocarbon emollient, and a surfactant having an HLB of greater than 10. The compositions are not taught to include alkyl-substituted polydimethylsiloxanes.

SUMMARY OF THE INVENTION

The present invention relates to antiperspirant/deodorant compositions comprising:

(a) from about 0.01% to about 60% by weight of an antiperspirant/deodorant active selected from antiperspirant actives, deodorant actives, perfumes, and combinations thereof;

(b) from about 30% to about 75% of a volatile fluid;

(c) from about 0.5% to about 25% of a wax structurant;

(d) from about 0.5% to about 15% of a $C_6$–$C_{45}$ alkyl-substituted polydimethylsiloxane; and (e) from about 0.5% to about 15% of a botanical extract, preferably a water-based botanical extract.

All percentages and ratios given herein are "by weight" unless otherwise specified.

All patents and publications referred to in this application are incorporated herein by reference, unless otherwise specified.

DETAILED DESCRIPTION OF THE INVENTION

The antiperspirant/deodorant compositions of the present invention include an antiperspirant/deodorant active, a volatile fluid, a wax structurant, $C_6$–$C_{45}$ alkyl-substituted polydimethylsiloxane, and a water-based botanical extract, such as ginger root extract. The compositions may optionally contain additional components conventionally found in topical antiperspirant/deodorant compositions at their art-established levels for their art-intended purposes. Examples of such optional components include fumed silica (used as a thickener) and silicone elastomers or high molecular weight (mw>200,000) polydimethylsiloxanes (used to enhance the aesthetics of the compositions). Each of those components, as well as the methods of making and using the compositions of the present invention, will be discussed in detail below. The compositions of the present invention permit the incorporation of aqueous-based components into normally anhydrous products without adversely affecting the viscosity, structural integrity and skin whitening characteristics of those products.

The present invention is particularly useful for formulating solid or semi-solid (e.g., cream, soft solid) compositions.

The compositions of the present invention include from about 0.01% to about 60% by weight of an antiperspirant/deodorant active selected from antiperspirant actives, deodorant actives, perfumes and combinations of those materials.

Those compositions of the present invention intended for use as an antiperspirant composition include an antiperspirant active suitable for application to human skin. The active may be dissolved in a solvent or dispersed throughout the composition as unsolubilized or partially unsolubilized solids. The concentration of the antiperspirant active in the composition should be sufficient to provide the desired perspiration wetness control and/or odor control from the antiperspirant formulation selected.

The antiperspirant embodiments of the present invention comprise antiperspirant actives at concentrations of from about 0.01% to about 60%, more preferably from about 2% to about 30%, by weight of the composition. These weight percentages are calculated on an anhydrous metal salt basis exclusive of water and any complexing agents such as glycine, glycine salts, or other complexing agents. The antiperspirant active as formulated in the composition is preferably in the form of dispersed solids having a preferred average particle size or diameter of less than about 100 $\mu$m, preferably less than about 50 $\mu$m. Also preferred are dispersed solid particulates having an average particle size or diameter of less than about 1 $\mu$m, even more preferably less than about 0.4 $\mu$m, and most preferably less than about 0.2 $\mu$m.

The antiperspirant active for use in the antiperspirant embodiments of the present invention include any compound, composition or other material having antiperspirant activity. Preferred antiperspirant actives include the astringent metallic salts, especially the inorganic and organic salts, of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant embodiments include those which conform to the formula:

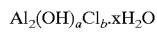

$$Al_2(OH)_aCl_b \cdot xH_2O$$

wherein a is about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones, et al., issued Sep. 9, 1975; U.S. Pat. No. 4,359,456, Gosling, et al., issued Nov. 16, 1982; and British Patent Specification 2,048,229, Fitzgerald, et al., published Dec. 10, 1980, all of which are incorporated herein by reference. Mixtures of aluminum salts are described in British Patent Specification 1,347,950, Shin, et al., published Feb. 27, 1974, which is also incorporated herein by reference.

The antiperspirant embodiments of the present invention contain from about 5% to about 35%, preferably from about 15% to about 26%, by weight of a particulate antiperspirant material. These weight percentages are calculated on an anhydrous metal salt basis (exclusive of glycine, the salts of glycine, glycols, or other complexing agents). The particulate antiperspirant material preferably has a particle size ranging about 1 to about 100 microns, more preferably from about 1 to about 45 microns. They may be impalpable (micronized) or microspherical in form. Any particulate antiperspirant materials known in the art may be used in the present invention. Such materials include, for example, many aluminum or zirconium astringent salts or complexes. Examples of useful antiperspirant materials are described in U.S. Pat. No. 6,287,544, Franklin, et al., issued Sep. 11, 2001; U.S. Pat. No. 6,261,543, Fletcher, et al., issued Jul. 17, 2001; and U.S. Pat. No. 6,187,301, Scavone, et al., issued Feb. 13, 2001, all incorporated herein by reference.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6 (x and y do not need to be integers); and where X is from about 1 to about 6. Aluminum salts of this type can be prepared in the manner described more fully in U.S. Pat. No. 3,887,692, Gilman, issued Jun. 3, 1975, and U.S. Pat. No. 3,904,741, Jones and Rubino, issued Sep. 9, 1975, incorporated herein by reference.

Preferred zirconium salts for use in the antiperspirant embodiments include those which conform to the formula:

$$ZrO(OH)_{2-a}Cl_a \cdot xH_2O$$

wherein a is from about 1.1 to about 2.0; x is from about 1 to about 8; and wherein a and x may both have non-integer values.

These zirconium salts are described in Belgian Patent 825,146, Schmitz, issued Aug. 4, 1975, which is incorporated herein by reference. Particularly preferred zirconium salts are those complexes which additionally contain aluminum and glycine, commonly known as "ZAG" complexes. These ZAG complexes contain aluminum chlorhydroxide and zirconyl hydroxychloride conforming to the above-described formulas. Such ZAG complexes are described in U.S. Pat. No. 3,679,068, Luedders, et al., issued Feb. 12, 1974; Great Britain Patent Application 2,144,992, Callaghan, et al., published Mar. 20, 1985; and U.S. Pat. No. 4,120,948, Shelton, issued Oct. 17, 1978, all of which are incorporated herein by reference.

The compositions of the present invention also include deodorant embodiments which contain a deodorant active, perfume or combinations of those materials, at concentrations ranging from about 0.01% to about 60%, preferably from about 0.01% to about 20%, more preferably from about 0.01% to about 10%, and even more preferably from about 0.1% to about 0.5%, by weight of the composition. These deodorant actives and perfumes include any known or otherwise safe and effective deodorant active or perfume suitable for topical application to human skin.

Deodorant actives suitable for use in the deodorant embodiments of the present invention include any topical material that is known for or is otherwise effective in preventing or eliminating malodor associated with perspiration. These deodorant actives are typically antimicrobial agents (e.g., bactericides or fungicides), malodor-absorbing materials, or combinations thereof.

Preferred deodorant actives are antimicrobial agents, non-limiting examples of which include acetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, phenoxyethanol, and combinations thereof.

Preferred deodorant actives are triclosan, triclocarban and combinations thereof, wherein the preferred concentration of either triclosan or triclocarban ranges from about 0.01% to about 10%, more preferably from about 0.1% to about 5%, even more preferably from about 0.1% to about 3%, by weight of the composition, and wherein the total concentration of triclosan and triclocarban when used together in a composition ranges from about 0.01% to about 2%, more preferably from about 0.2% to about 1%, even more preferably from about 0.2% to about 0.6%, by weight of the composition.

Other deodorant actives include odor-absorbing materials such as carbonate and bicarbonate salts, including alkali metal carbonates and bicarbonates, ammonium and tetraalkylammonium. Preferred are sodium and potassium salts of such odor-absorbing materials. Still other deodorant actives include the antiperspirant actives described hereinbefore.

Perfumes suitable for use in the deodorant embodiments of the present invention include any perfume material that can be applied to the skin and is known for or is otherwise effective in masking malodor associated with perspiration, or which otherwise provides the composition with the desired perfumed aroma. These include any perfume or perfume chemical, including pro-perfumes and deo-perfumes, suitable for topical application to the skin.

The amount or concentration of the perfume in the deodorant embodiments should be effective to provide the desired aroma characteristics or to mask malodor, wherein the malodor is inherently associated with the composition itself or is associated with malodor development from human perspiration.

Perfumes are made by those skilled in the art in a wide variety of fragrances and strengths. Typical perfumes and fragrances are described in Arctander, Perfume and Flavour Chemicals (Aroma Chemicals), Vol. I and II (1969); and Arctander, Perfume and Flavour Materials of Natural Origin (1960); U.S. Pat. No. 4,322,308; U.S. Pat. No. 4,304,679; U.S. Pat. No. 5,554,588; U.S. Pat. No. 4,278,658; U.S. Pat. No. 5,501,805; and EP Patent Application 684 037 A1; all of which are incorporated herein by reference.

The present invention also contains from about 30% to about 75%, preferably from about 40% to about 60%, by weight of a volatile fluid compatible with the other antiperspirant/deodorant composition ingredients and suitable for application to human skin. Preferred materials of this class include volatile hydrocarbon solvents (such as dodecene, isodecene, hydrogenated polydecene, polydecene, and isohexadecene) and volatile silicone solvents, both of which are well known for use in cosmetic and deodorant sticks and may be used herein. Volatile silicones known for use in deodorant sticks are preferred for use in the present invention. The volatile silicone material is preferably a cyclic or a linear polydimethylsiloxane.

The cyclic polydimethylsiloxanes preferably include from about 3 to about 7 silicon atoms, more preferably from about 4 to about 6 silicon atoms. The general formula for such siloxanes is:

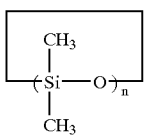

wherein n is from about 3 to about 7. The linear volatile polydimethylsiloxanes contain from about 3 to about 9 silicon atoms and have the general formula:

wherein n is from about 1 to about 6.

Silicones of the above type are commercially available, for example, from Dow Corning Corporation (Dow Corning 344, 345, 200 and 1184 fluids), Union Carbide (Silicone 7207 and Silicone 7158), and Stauffer Chemical (SWS-03314), as well as from General Electric Specialty Chemicals (SF-1202).

The linear volatile silicone materials generally have viscosities of less than about 5 centistokes at 25° C., while the cyclic materials have viscosities less than about 10 centistokes. "Volatile" means that the material has a measurable vapor pressure. A description of volatile silicones is found in Todd and Byers, "Volatile Silicone Fluids for Cosmetics", Cosmetics and Toiletries, 91:27–32 (1976), incorporated herein by reference.

Cyclic polydimethylsiloxanes, and particularly cyclomethicone D-5 (decamethylcyclopentasiloxane) and D-6 (dodecamethylcyclohexasiloxane), are preferred for use in the compositions of the present invention.

The compositions of the present invention contain from about 0.5% to about 25%, preferably from about 5% to about 17%, of a wax structurant material. These materials may be high melting point waxes or low melting point waxes, although the high melting point waxes are preferred. The low melting pointing waxes have a melting point of from about 37° C. to about 65° C., and the high melting point waxes have a melting point of from about 65° C. to about 102° C., preferably from about 65° C. to about 80° C.

Illustrative high melting point waxes include beeswax, spermaceti, carnauba, baysberry, candulilla, montan, ozokerite, ceresin, paraffin, castor wax, synthetic waxes such as Fisher-Tropsch waxes, microcrystalline waxes, ethylene glycol diesters, triglyceride waxes and ethylene/vinyl acetate copolymers, jojoba esters (such as Floroesters 30, 50, 60 and 70), and mixtures thereof. Castor wax is a preferred material. Specific castor waxes illustratively include MP-80 and MP-70. As indicated previously, beeswax, carnauba wax, or other natural waxes and petroleum-based waxes may be used in place of (or in addition to) the castor wax. In addition, derivatized waxes, such as hexanediol behenyl beeswax (Koster Keuunen), silicone waxes, such as stearoxytrimethylsilane, an example of which is DC 580 (made by Dow Corning), and synthetic wax, such as Syncrowax HGL-C ($C_{18}$–$C_{36}$ mixed acid triglycerides, commercially available from Croda), can be used as the high melting point wax. Preferred wax structurants are $C_{20}$–$C_{40}$ hydrocarbon waxes. A particularly preferred high melting point wax for use in the present invention is behenyl alcohol (n-$C_{22}$ alcohol).

Low melting point waxes usable in the present invention include fatty acids, fatty alcohols, fatty acid esters and fatty acid amides, having fatty chains of from about 8 to about 30 carbon atoms, preferably from about 12 to about 18 carbon atoms, and mixtures thereof. Illustrative low melting point waxes include cetyl alcohol, myristyl alcohol, stearyl alcohol, behenyl alcohol, arachidyl alcohol, palmitic acid, paraffin, cetyl stearate, cetyl palmitate, cetyl myristate, stearyl stearate, and mixtures thereof. Also illustrative of the low melting point waxes are silicone waxes, such as stearoxy dimethicone.

The $C_6$–$C_{45}$ alkyl-substituted polydimethylsiloxane materials utilized in the present invention are included at from about 0.5% to about 15%, preferably from about 1% to about 5%, of the total composition. The materials are described in U.S. Pat. No. 5,939,056, Fletcher, et al., issued Aug. 17, 1999; U.S. Pat. No. 5,225,188, Abrutyn, et al., issued Jul. 6, 1993; EP Patent Application 549 223, Dow Corning; and U.S. Pat. No. 6,258,365 B1, LeGrow, et al., issued Jul. 10, 2001, all of which are incorporated herein by reference. The polyalkylmethylsiloxane waxes for use in the present invention have the general formula:

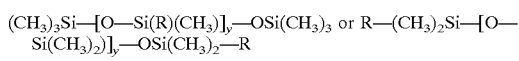

In the above formula, y is from about 1 to about 80 and R is a straight or branched chain alkyl group containing from about 6 to about 45 carbon atoms, preferably from about 16 to about 30 carbon atoms. Preferred materials for use in the present invention include $C_{16}$–$C_{30}$ alkyl polydimethylsiloxanes, preferably $C_{20}$–$C_{30}$ alkyl polydimethylsiloxanes, more preferably $C_{24}$–$C_{28}$ alkyl polydimethylsiloxanes.

The final required component in the compositions of the present invention is from about 0.5% to about 15%, preferably from about 0.5% to about 10%, more preferably from about 1% to about 7.5%, of a botanical extract which is compatible with the skin and with the remainder of the deodorant/antiperspirant formulation, and which provides a cosmetic or aesthetic benefit to the skin. The botanical extracts useful herein are generally produced by aqueous, glycolic, liquefied gas (super critical extraction) or hydroalcoholic extraction of the plant material. This is done by extracting the plant material with a solvent at room temperature, chilled or heated, or extracting using soxhlet extraction or steam distilled or pressed, resulting in an aqueous or hydroalcoholic, or polyol solution that can also be supplied as a dried powder. Non-limiting examples of solvents usable for extraction include water, alcohol (e.g., methanol, ethanol, propanol), polyhydric alcohols (e.g., glycerin, propylene glycol, tripropylene glycol, butylene glycol, PEG-8), ketones (e.g., acetone), esters (e.g., ethyl acetate), cyclic ethers, halogenated hydrocarbons, polyethers (e.g., polyethylene glycol, polyoxyethylene), aromatic hydrocarbons, cyclomethicone, linear dimethicones, and liquefied carbon dioxide. Examples of plant extracts which can be used in the present invention include ginger rhizome, almond, birch, clove, rose hip, white birch, gambi, burnet, hiba, willow herb, *Phellodendron Amurense, Coptis Chinesis*, clove oil extract, tea tree oil, olive leaf extract, rosemary extract, fennel seed, phytoplenolin, sericin, K2 glycerrizinate, capsaicin, menthol, and menthyl lactate. The preferred botanical extracts are present in a water-based solution. Preferred materials include ginger extract, burnet extract, and mixtures of those materials. A particularly preferred material is ginger root extract (*Zingiber Officinale*), which can reduce the diameter and length of underarm hair and therefore decrease the amount of shaving required by the user.

The present invention allows for the incorporation of water-based materials into an anhydrous antiperspirant/deodorant system. In fact, the compositions of the present invention can include up to about 15% water.

The compositions of the present invention may also contain optional components conventionally used in antiperspirant or deodorant compositions which modify the physical characteristics of the compositions or components of those compositions or serve as "active" components when deposited on the skin in addition to the antiperspirant or deodorant material. Optional components useful herein are described in the following documents, all incorporated by herein by reference: U.S. Pat. No. 4,049,792, Elsnau, issued Sep. 20, 1977; Canadian Patent 1,164,347, Beckmeyer et al., issued Mar. 27, 1984; EP Patent Application 117 070, May, published Aug. 29, 1984; and Geria, "Formulation of Stick Antiperspirants and Deodorants", Cosmetics and Toiletries, 99:55–60 (1984).

The specific nonactive components that may be used in the present invention will depend upon the characteristics desired for the particular compositions. These components are used at their art-established levels to achieve their art-established benefits. Such components include, for example, emollients, colorants, perfumes, emulsifiers, surfactants, preservatives, and skin feel enhancers.

The compositions may, for example, optionally contain from about 0.5% to about 10% of an additional structurant material selected from polyethylene, clay, talc, starch, and silica, as well as mixtures of those materials. The preferred additional structurant material is silica.

A number of fumed silica products are available commercially. These include such materials as Cab-O-Sil™ (Cabot), Optigel and Tixogel (Süd-Chemie Rheologicals), and Aerosil 200™ (Degussa). Silica is the inorganic oxide that conforms to the formula $SiO_2$. Precipitated silicas are available commercially as Syloid™ silicas (W. R. Grace & Co.) and Silcrons™ (Glidden Pigments).

Clay materials which may be used in the present invention as optional thickeners include hydrophobic bentonites and hectorites. Bentone™ (Elementis Specialties, formerly Rheox and NL Industries) is a tradename of hydrophobic bentonites and hectorites. Bentone is prepared by reacting bentonite in a cation exchange system with an amine. Different amines are reacted to obtain a variety of Bentones. Specific examples of Bentones include Bentone 38, Bentone 34, and Bentone 27, Tixogel OMS, Tixogel USP and Tixogel FTN. They are available commercially from Elementis Specialties and Süd-Chemie Rheologicals.

The compositions of the present invention may also optionally contain high molecular weight silicone to provide aesthetic benefits for the formulations. Such materials are generally present at from about 0.1% to about 10% of the composition. Examples of such high molecular weight silicones are well known in the art and include, for example, dimethicone copolyol (e.g., Shin Etsu KF 6017, Dow Corning 5200), cross-linked silicone elastomers (e.g., Dow Corning 9040 and 9011, Shin Etsu KSG 30, KSG 21, KSG 210, KSG 15AP), and silicone gums (e.g., Dow Corning 1502, Shin Etsu MK 15H). Polydiorganosiloxane-polyoxyalkylene copolymers (dimethicone polyols), are well known in the cosmetics and personal care arts and are described, for example, in U.S. Pat. No. 4,265,878, incorporated herein by reference, which further describes the copolymers and their methods of preparation. Briefly, polydiorganosiloxane-polyoxyalkylene copolymers are characterized by at least one polydiorganosiloxane segment and at least one polyoxyalkylene segment. The polydiorganosiloxane segment consists essentially of $R_nSiO_{(4-n)}$ units wherein n has a value of from 0 to 3 inclusive. There is an average of approximately two R radicals per siloxane unit in the copolymer with each R denoting a radical selected from the group consisting of methyl, ethyl, vinyl, phenyl and a divalent radical bonding the polyoxyalkylene segment to the polydiorganosiloxane segment. Useful polyoxyalkylene segments have an average molecular weight of from about 1000 to about 5000 and consist of from 0 to about 60 mole % polyoxypropylene units and from about 40 to about 100 mole % polyoxyethylene units. Polyoxyalkylene segments consisting of from about 40 to about 60 mole % of polyoxypropylene units and from about 40 to about 60 mole % of polyoxyethylene units are more preferred with segments consisting of an equimolar mixture of polyoxypropylene and polyoxyethylene units being most preferred. A terminal portion of each polyoxyalkylene segment is bonded to the polydiorganosiloxane segment.

For example, a preferred copolymer, with a weight ratio of about 2.8 polydiorganosiloxane segments to polyoxyalkylene segments, is characterized by the average formula:

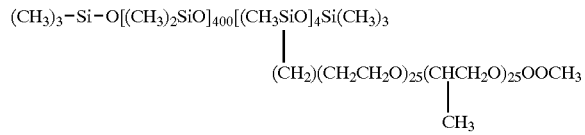

The crosslinked siloxane elastomers are also well known in the cosmetic formulational arts. They are disclosed, for example, in U.S. Pat. No. 5,942,215, Edwards et al., issued Aug. 24, 1999, incorporated herein by reference. Siloxane elastomers are crosslinked or partially crosslinked, entangled, viscoelastic polymer networks, preferably made by the platinum catalyzed reaction known as hydrosilation of vinyl silicone fluids by either hydrosiloxane fluids or highly branched MQ hydride fluids. Control of the stoichiometry and type of the vinyl silicone fluid and the silanic crosslinker controls the properties of the cured networks. Additional vinyl reactants, such as vinyl alkenes can be introduced in the reactive medium to further modify the silicone network. The choice of the reaction solvent is also a means to modify the properties of the resultant materials. The average molecular weight of the silicone elastomers is between about 10,000 and about 40 million, and is preferably between about 10,000 and about 20 million. Typically, the crosslinked siloxane polymeric networks are swollen substantially by oily materials, preferably silicone fluids such as cyclomethicone and/or dimethicone.

Preferred crosslinked silicone materials are described in U.S. Pat. No. 5,654,362, Schulz, Jr., et al., issued Aug. 5, 1997, incorporated herein by reference. An example of such a material is Dow 9040, commercially available from Dow Corning Corporation, Midland, Mich.

The compositions of the present invention may also include a non-toxic, water-insoluble, occlusive, film-forming polyester polymer material. The polyester polymer is one which forms a film on the skin upon evaporation of the volatile solvent; the film provides an occlusive barrier on the skin. The polyester material must be non-toxic and non-irritating to the skin and it must be compatible with the other components included in the antiperspirant composition. When used, the polyester polymer is included in the compositions at levels from about 0.5% to about 10%, preferably from about 1% to about 7.5%, more preferably from about 1% to about 5%, by weight of the compositions. These materials can enhance both the efficiency and the aesthetics of the compositions.

A preferred group of polyester materials includes a backbone derived from the reaction of a linear or branched-chain multifunctional hydroxy-containing reactant (i.e., diols, polyols, carbohydrates, preferably a diol) with a linear or branched chain multifunctional carboxylic acid or anhydride (preferably a diacid). They can be further end-capped with a monofunctional acid or hydroxy-containing component. Such polymers typically have a molecular weight of from about 500 to about 1,000,000.

Preferred carboxylic acids or anhydrides for use in forming these polymers include adipic acid, succinic acid or anhydride, sebasic acid or anhydride, phthalic acid or anhydride, isophthalic acid, tetraphthalic acid, pyromellitic anhydride or dianhydride, trimellitic anhydride, and mixtures of these materials.

Preferred multifunctional hydroxy-containing compounds for use in forming these polymers include propylene glycol, dipropylene glycol, butanediol, tripropylene glycol, hexanediol, polyoxyethylene glycol, neopentyl glycol, trimethylpetanediol, pentaerythritol, dipentanerythritol, glycerin, methyl glucoside, sucrose, and mixtures of these materials.

Particularly preferred materials are those commercially available under the tradename Lexorez TC-8 and TC-15, commercially available from Inolex. These materials are described in U.S. Pat. No. 5,880,250, Housel et al., issued Mar. 9, 1999, and U.S. Pat. No. 6,103,822, Housel et al., issued Aug. 22, 2000, both incorporated herein by reference. Lexorez TC-8 and TC-15 are trimethylpentanediol/adipic acid/isononanic acid copolymers. Lexorez TC-8 is a trimethylpentanediol/adipic acid copolymer. Without intending to be bound by theory, it is believed that a film is formed by the polyester polymer on the surface of the skin upon evaporation of the volatile solvent. This film acts as an occlusive barrier for the antiperspirant active on the skin, which enhances the efficacy of that active.

The antiperspirant compositions of the present invention may be manufactured using methods known in the art. For example, soft-solid (cream) compositions of this invention can be produced by processes which involve forming a heated mixture of the composition at a temperature such that the structurant is in solution in the topical volatile carrier phase, pouring that mixture into a mold, which may take the form of a dispensing container, and then cooling the mixture whereupon the structurant solidifies within the carrier phase and thereby gels that phase and hence the whole composition.

A preferred method for processing the antiperspirant/deodorant cream compositions described herein utilizes conventional processes for cream compositions followed by a solidification step. A conventional process sequence for cream antiperspirant formulations comprises first mixing a thickener material with the topical volatile carrier. Typically, some type of homomixing is needed to form a homogenous mixture. The structurant or mixture of structurants, namely the wax(es) and, if included, the film-forming polyester polymer are then blended into the topical carrier mixture at a temperature that is high enough to melt the structurant. Thereafter, particulate antiperspirant active can be blended with the carrier solution and mixed until homogenous. Emollients, essential and optional components are blended into the carrier solution. Processing temperatures will generally range from about 50° C. to about 125° C. After the mixture is homogenous, the resulting mixture is introduced into a dispensing container, such as a dispensing canister. This is usually carried out at a temperature of 5° to 30° C. above the setting temperature of the composition. The container and contents are then cooled to ambient temperature. Cooling may be brought about by nothing more than allowing the container and contents to air cool. Cooling may be assisted by blowing ambient or even refrigerated air over the containers and their contents.

The antiperspirant/deodorant suspension solid stick compositions described herein can be produced by conventional processes for suspension solid stick compositions followed by a solidification step. A conventional process sequence for suspension antiperspirant formulations comprises first mixing the structurant or mixture of structurants, namely the wax (es) and, if utilized, the film-forming polyesters polymer, with the topical volatile carrier at a temperature that is high enough to melt the structurant. Thereafter, particulate antiperspirant active can be blended with the carrier solution and mixed until homogenous. Thickeners, emollients, essential and optional components are blended into the carrier solution. Processing temperatures will generally range from about 50° C. to about 125° C. The suspension solid stick compositions are formed into a solid mass by cooling, for example by being introduced into its dispensing container at a temperature that is often 50° to 10° C. above its normal setting temperature. The process normally includes a suitable filling process, such as a pour fill process (sometimes gravity-fed injection) or injection at elevated pressure into a dispensing container, such as a barrel, where it is cooled or allowed to cool to ambient. Cooling may be brought about by nothing more that allowing the container and contents to air cool. Cooling may be assisted by blowing ambient or even refrigerated air over the containers and their contents.

The antiperspirant compositions of the present invention are used in a conventional manner. Specifically, the compositions may be used to prevent and/or control perspiration wetness or body odor by topically applying, one or more times a day, an effective amount of the composition to areas of the body particularly prone to perspiration or odor (for example, the underarm area).

The following nonlimiting examples illustrate the compositions, method of making, and methods of using the present invention described in this application.

EXAMPLES

Antiperspirant stick and soft solid compositions of the present invention, having the compositions given in the table below, are formulated using the procedures described above. The compositions are stable, provide good antiperspirant performance with good skin feel and minimized skin whitening, effectively incorporate the water-containing botanical extract component, have minimized syneresis upon storage, and leave the skin with a good cosmetic feel.

Antiperspirant Solid Stick Compositions

| | Example | | | |
|---|---|---|---|---|
| Ingredient Name | 1 % | 2 % | 3 % | 4 % |
| Cyclomethicone | 47.2 | 45.0 | 52.1 | 51.0 |
| Hydrogenated Polydecene | 5.3 | | 4.4 | |
| Isododecane | | 4.0 | | |
| Behenyl Alcohol | 12.5 | 12.5 | 5.0 | 12.5 |
| C24–28 Alkyl Methicone | 2.0 | 1.75 | 2.0 | 2.0 |
| Dimethicone Crosspolymer | 1.0 | 0.75 | | 2.0 |
| Isostearyl Benzoate | | | 2.0 | |
| Trimethylpentanediol/Adipic Acid/ | | | | 1.0 |

-continued

| | Example | | | |
|---|---|---|---|---|
| Ingredient Name | 1 % | 2 % | 3 % | 4 % |
| Isononanoic Acid Copolymer | | | | |
| Di PPG-2 Myreth-10 Adipate | 2.0 | 1.5 | | |
| Polyethylene | | | 5.0 | 2.5 |
| Colloidal Silicone Dioxide | 2.0 | 2.5 | 2.5 | |
| Corn Starch Modified | 1.0 | 1.0 | | |
| Aluminum Zirconium Tetrachlorohydrex-Gly | 24.0 | 24.0 | 24.0 | 24.0 |
| Aqueous Solution of Ginger Root Extract | 3.0 | 7.0 | 3.0 | 5.0 |
| Fragrance | q.s. | q.s. | q.s. | q.s. |
| TOTAL | 100.0 | 100.0 | 100.0 | 100.0 |

Antiperspirant Soft Solid Compositions

| | Example | | |
|---|---|---|---|
| Ingredient Name | 5 % | 6 % | 7 % |
| Cyclomethicone | 46.5 | 46.1 | 51.9 |
| Hydrogenated Polydecene | | 17.0 | 6.9 |
| Isododecane | 7.0 | | |
| Behenyl Alcohol | 5.0 | 5.1 | 5.5 |
| C24–28 Alkyl Methicone | 2.0 | 2.3 | 2.0 |
| Dimethicone Crosspolymer | | | 1.2 |
| Isostearyl Benzoate | 1.0 | | |
| Trimethylpentanediol/Adipic Acid/ Isononanoic Acid Copolymer | 1.0 | | |
| Colloidal Silicone Dioxide | 2.5 | 2.5 | 2.5 |
| Corn Starch Modified | 4.0 | | 1.0 |
| Aluminum Zirconium Tetrachlorohydrex-Gly | 24.0 | 24.0 | 24.0 |
| Aqueous Solution of Ginger Root Extract | 7.0 | 3.0 | 5.0 |
| Fragrance | q.s. | q.s. | q.s. |
| TOTAL | 100.0 | 100.0 | 100.0 |

What is claimed is:

1. A water-containing antiperspirant/deodorant composition in the form of a solid or semi-solid, comprising:
   (a) from about 0.1% to about 60% by weight of an antiperspirant/deodorant active selected from antiperspirant actives, deodorant actives, perfumes, and combinations thereof;
   (b) from about 30% to about 75% of a volatile fluid;
   (c) from about 0.5% to about 25% of a wax structurant;
   (d) from about 0.5% to about 15% of a $C_6$–$C_{45}$ alkyl substituted polydimethylsiloxane; and
   (e) from 0.5% to about 15% of a botanical extract.

2. The antiperspirant/deodorant composition according to claim 1 which includes a deodorant active selected from antimicrobial agents, deodorant perfumes, malodor absorbing agents, and combinations of those materials.

3. The antiperspirant/deodorant composition according to claim 2 wherein the deodorant active is an antimicrobial agent comprising from about 0.01% to about 10% of the composition.

4. An antiperspirant/deodorant composition according to claim 3 wherein the antimicrobial agent is selected from triclosan, triclocarban, and mixtures thereof.

5. The antiperspirant/deodorant composition according to claim 1 wherein the active material is a particulate antiperspirant active.

6. The antiperspirant/deodorant composition according to claim 5 wherein the volatile fluid is selected from volatile hydrocarbons, volatile silicones, and mixtures thereof.

7. The antiperspirant/deodorant composition according to claim 6 wherein the wax structurant is selected from $C_{20}$–$C_{40}$ hydrocarbon waxes.

8. The antiperspirant/deodorant composition according to claim 7 wherein the volatile fluid is selected from dodecene, isodecene, hydrogenated polydecene, polydecene, isohexadecene, D5 cyclomethicone, D6 cyclomethicone, and mixtures thereof.

9. The antiperspirant/deodorant composition according to claim 7 wherein the volatile fluid is selected from linear polydimethylsiloxanes containing from about 3 to about 9 silicon atoms, cyclic polydimethylsiloxanes containing from about 3 to about 7 silicon atoms, and mixtures thereof.

10. The antiperspirant/deodorant composition according to claim 9 which comprises from about 2% to about 30% of an antiperspirant active material.

11. The antiperspirant/deodorant composition according to claim 9 wherein the antiperspirant active material is selected from aluminum and zirconium polymer materials.

12. The antiperspirant/deodorant composition according to claim 11 wherein the alkyl-substituted polydimethylsiloxane is selected from $C_{16}$–$C_{30}$ alkyl polydimethylsiloxane materials.

13. The antiperspirant/deodorant composition according to claim 12 wherein the volatile fluid is selected from cyclic polydimethylsiloxanes containing from about 3 to about 7 silicon atoms.

14. The antiperspirant/deodorant composition according to claim 13 which comprises from about 40% to about 60% of the volatile fluid component.

15. The antiperspirant/deodorant composition according to claim 13 which comprises from about 1% to about 5% of the alkyl-substituted polydimethylsiloxane component.

16. The antiperspirant/deodorant composition according to claim 13 which comprises from about 5% to about 17% of the wax structurant component.

17. The antiperspirant/deodorant composition according to claim 13 wherein the alkyl-substituted polydimethylsiloxane component is selected from $C_{24}$–$C_{28}$ alkyl polydimethylsiloxanes.

18. The antiperspirant/deodorant composition according to claim 13 wherein the wax structurant is behenyl alcohol.

19. The antiperspirant/deodorant composition according to claim 13 which comprises from about 1% to about 7.5% of the botanical extract component.

20. The antiperspirant/deodorant composition according to claim 13 wherein the botanical extract is selected from ginger root extract, burnet extract, and mixtures thereof.

21. The antiperspirant/deodorant composition according to claim 13 which comprises from about 40% to about 60% of the volatile fluid component, from about 1% to about 5% of the $C_{24}$–$C_{28}$ alkyl polydimethylsiloxane component, from about 5% to about 17% of the behenyl alcohol wax structurant component, and from about 1% to about 7.5% of ginger root extract.

22. The antiperspirant/deodorant composition according to claim 13 which additionally comprises from about 1% to about 10% of an additional structurant selected from polyethylene, clay, talc, starch, silica, and mixtures thereof.

23. The antiperspirant/deodorant composition according to claim 22 wherein the additional structurant component is silica.

24. The antiperspirant/deodorant composition according to claim 13 which additionally comprises from about 0.1% to about 10% of a high molecular weight silicone component.

25. The antiperspirant/deodorant composition according to claim 1 wherein the botanical extract is a water-based extract.

26. The antiperspirant/deodorant composition according to claim 19 wherein the botanical extract is a water-based extract.

27. The antiperspirant/deodorant composition according to claim 21 wherein the botanical extract is a water-based extract.

28. The antiperspirant/deodorant composition according to claim 1 wherein the botanical extract is selected from ginger rhizome, almond, birch, clove, rose hip, white birch, gambi, burnet, hiba, willow herb, *Phellodendron amurense, Coptis chinesis*, clove oil extract, tea tree oil, olive leaf extract, rosemary extract, fennel seed, phytoplenolin, sericin, K2 glycerrizinate, capsaicin, menthol and menthyl lactate, and mixtures thereof.

\* \* \* \* \*